United States Patent [19]

Wilson

[11] 4,387,472
[45] Jun. 14, 1983

[54] TORQUE ABSORBER WITH BIOFEEDBACK

[75] Inventor: Michael T. Wilson, Missouri City, Tex.

[73] Assignee: Medical Center Prosthetics, Inc., Houston, Tex.

[21] Appl. No.: 193,129

[22] Filed: Oct. 2, 1980

[51] Int. Cl.³ .......................... A61F 1/04; A61F 1/08; G08B 23/00
[52] U.S. Cl. .............................................. 3/32; 3/1.1; 3/2; 128/779; 340/573
[58] Field of Search .................. 3/1, 1.1, 2, 21, 30–35; 128/779, 774, 782; 73/172; 340/573

[56] References Cited

U.S. PATENT DOCUMENTS

| | | | |
|---|---|---|---|
| 2,567,066 | 9/1951 | Goldman | 3/1.1 |
| 2,582,234 | 1/1952 | Conzelman et al. | 3/1.2 X |
| 3,509,583 | 5/1970 | Fraioli | 3/1.1 |
| 3,702,999 | 11/1972 | Gradisar | 340/573 |
| 3,706,465 | 12/1972 | Olowinski | 3/2 X |
| 3,751,733 | 8/1973 | Fletcher et al. | 3/1.1 |
| 3,982,280 | 9/1976 | Asbelle et al. | 3/32 |
| 4,134,159 | 1/1979 | Wilson | 3/2 |

FOREIGN PATENT DOCUMENTS 605612  5/1978  U.S.S.R. ................. 3/21

OTHER PUBLICATIONS

Undated Advertisement of Colmed Ltd., 330 Primrose Road, Suite 610, Burlingame, California 94010.
Vol. BME-26, No. 8, IEEE Transactions on Biomedical Engineering, Aug. 1979, pp. 450 and 456.
Bulletin of Prosthetic Research, Fall 1968.
Krusen Center for Research and Engineering Pamphlet Entitled "Limb Load Monitor", Moss Rehabilitation Hospital, Phila., PA.
"A Shorter Pylon Transducer for Measurement of Prosthetic Forces and Moments During Amputee Gait" by N. Berme et al., Engineering in Medicine, vol. 4, No. 4, pp. 6–8, 1976.

Primary Examiner—Ronald L. Frinks
Attorney, Agent, or Firm—Phillips, Moore, Lempio & Finley

[57] ABSTRACT

A two-element prosthesis is provided with a resilient connector that permits limited rotation of one element relative the other about the three axes of the two elements as defined by the junction of the two elements. The resilient connector further absorbs a limited amount of compressive shock transmitted from one element to the second element. The resilient member includes a sensing system that indicates a compressive force at the resilient member in excess of a predetermined amount.

18 Claims, 3 Drawing Figures

TORQUE ABSORBER WITH BIOFEEDBACK

BACKGROUND OF THE INVENTION

This invention relates to a prosthetic device. In particular it relates to a torque absorber and sensing element that permits limited movement of a joint between two prosthetic members while providing a signal upon an excessive compressive force between the two elements.

Following the amputation of a lower limb, it is important that the amputee be fitted with a prosthesis as early as possible in order to effect a rapid recovery and to provide early familiarity with the use of the prosthetic device. Due to the nature of amputation, the residual limb is particularly sensitive to the pressure of a prosthesis when initially fitted. In order to attain a balance between the sensitivity and the requirement for early fitting, the prosthetist will ordinarily fit the amputee with a temporary prosthetic device within a period of a few days following the amputation. It is not the intent of the prosthetist to have the patient become completely mobile on this temporary prosthesis; rather, it is the intent of the prosthetist to carry the patient through the healing stage of the residual limb in a partially ambulatory state. In the past, it has been the practice of the prosthetist to tell the patient not to exceed, for example, forty pounds of force on the residual limb when using the temporary prosthetic device. It is unrealistic to expect a new amputee to be able to sense a particular force in a residual limb, particularly when the residual limb is sensitive to undue pressure. As a result, a good deal of guesswork coupled with discomfort on the part of the patient has occurred in the fitting of prosthetic devices.

In addition to the problem of attempting to establish a maximum pressure on the residual limb, a new amputee needs a prosthetic device that is similar to the natural limb which has been removed. In particular, it is appropriate to provide a limited degree of flexibility at or in the vicinity of the missing joints, such as the knee and the ankle. During the temporary phase, that is, during the familiarization period with the temporary prosthetic device, it is appropriate to eliminate a fully operative knee joint as use of such a prosthetic knee requires a particular acquired skill. During the familiarization period, it is appropriate to reduce to a minimum the learning requirements, hence, eliminating the knee joint is appropriate. Nevertheless, the patient needs some motion between the residual stump and the bearing surface or floor. If there is no capability to rotate between the stump and the floor, the prosthesis will rub or chafe the residual limb to the point where blisters or ulcers are formed. Accordingly, there must be some flexibility. This is particularly important where the patient is in the preliminary or learning phases of adjustment to a prosthetic device. Such flexibility is described in U.S. Pat. No. 4,134,159, issued on Jan. 16, 1979 to the inventor herein. However, this torque absorber is normally located at the upper end of the prosthetic device, in particular between the socket and the upper pylon. Since this type of torque absorber is generally molded into the cosmesis, it is not appropriate for a temporary prosthetic device. Furthermore, this particular type of torque absorber is not appropriately combined with a pressure sensing system because of the nature of its structure.

Accordingly, it is an object of the present invention to provide a prosthesis of at least two elements that permits limited movement between the two elements.

It is a further object of this invention to provide a prosthesis that includes a pressure sensing system.

It is still another object of this invention to provide a prosthesis wherein a pressure sensing system is responsive to a predetermined pressure.

It is still further an object of this invention to provide a prosthesis which combines the motion of a torque absorber along with the pressure sensing capability.

It is also an object of this invention to provide adjustability to the pressure sensing system.

The present invention is directed to overcome one or more of the problems as set forth above and to meet at least the objects as set forth.

SUMMARY OF THE INVENTION

Broadly stated, the invention is a prosthesis comprising a first member and a second member. An interconnection device is included which connects and permits limited motion between the first and second member. A pressure responsive indicator responds to a predetermined force between the first and the second member.

DETAILED DESCRIPTION OF THE PREFERRED EMBODIMENT

Figure 1:
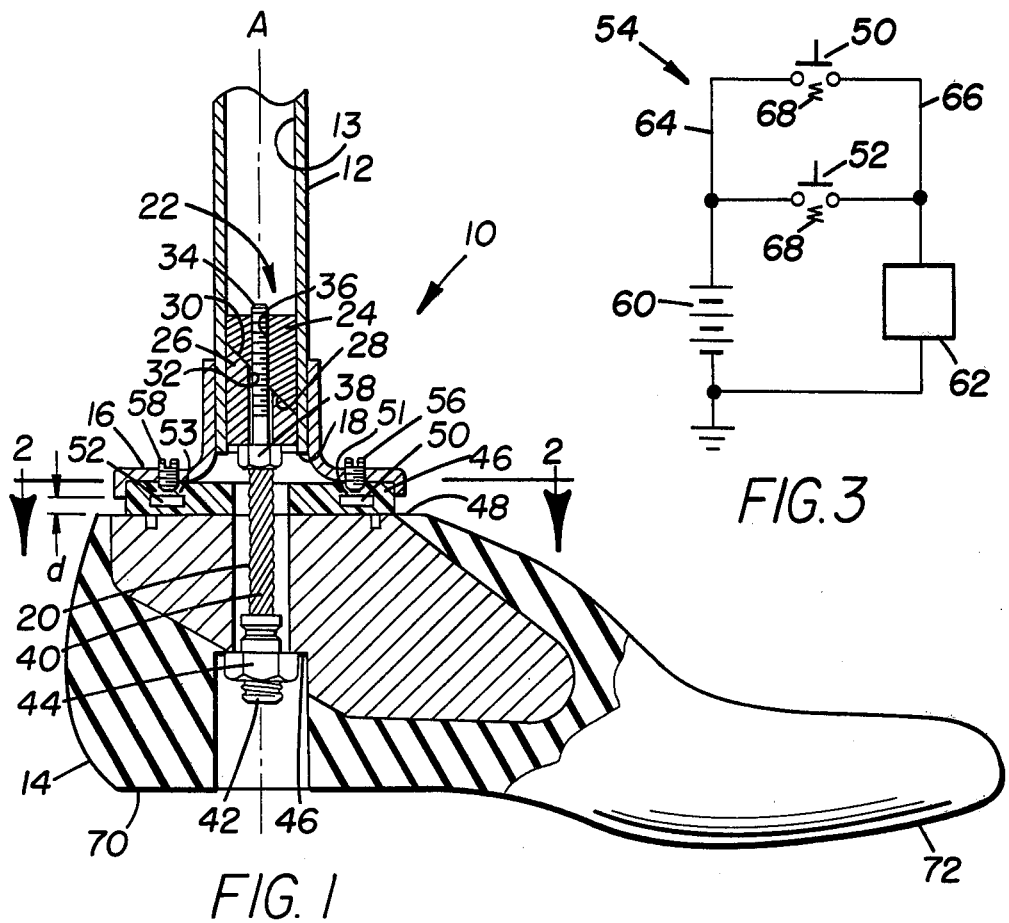
FIG. 1 is a view partly in section of an embodiment of the present invention showing a prosthetic foot and a prosthetic lower limb.

Referring to FIG. 1, a prosthesis 10 is shown partly in section. Prosthesis 10 consists of a first member such as pylon 12 and a second member such as foot 14. Means are provided to interconnect an endoskeletal prosthetic limb such as pylon 12 and foot 14 by a flange 16 fitted to end 18 of pylon 12. A flexible connector 20 is fixed at one end to pylon 12 and at its other end to foot 14, as can be seen in FIG. 1.

Connector 20 is fixed to pylon 12 by a wedging arrangement 22 which is relatively well known in the art. In particular, wedging member 22 includes a pair of ungula or cylindrical members 24 and 26, each having matching diagonal surfaces 28 and 30, respectively. Cylindrical member 26 has an axial bore 32 of sufficient diameter to slidingly receive a threaded member 34. Cylindrical member 24 has an axial threaded bore 36 adapted to threadably received threaded member 34. Threaded member 34 has formed at the end adjacent cylindrical member 26 an enlarged head, such as hexagonical head 38. With threaded member 34 threadably engaged in threaded bore 36 in the manner shown in FIG. 1, rotation of threaded member 34 will cause relative movement of cylindrical members 24 and 26 to the point where cylindrical member 24 and 26 will wedge in bore 13 of pylon 12.

Bondingly fixed to head 38 is a flexible member such as cable 40 that extends downwardly and has fixed at its opposite end by swaging or the like a threaded portion 42. Threaded portion 42 is adapted to receive a nut 44 which, with the prosthesis assembled, abuts a shoulder 46 of foot 14. Thus, with the connector 20 positioned in pylon 12 along with the foot 14 in the position shown in FIG. 1, the nut 42 may be tightened to hold the foot 14 in the position indicated.

Figure 3:
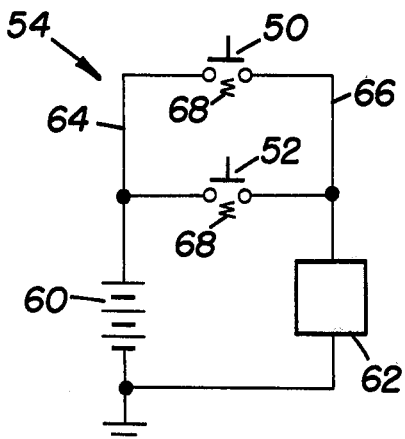
FIG. 3 is a schematic diagram of a circuit which provides the alarm capability of this invention.
Figure 2:
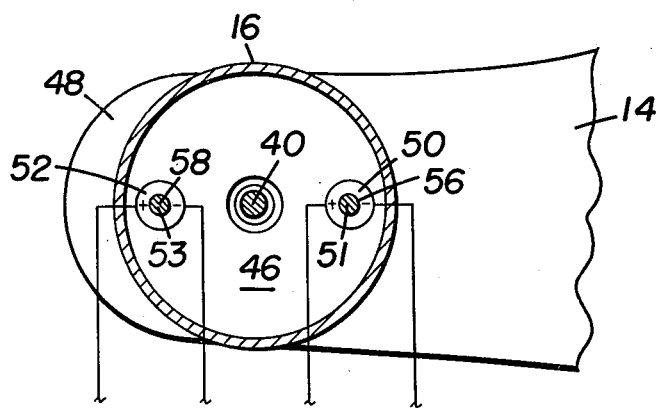
FIG. 2 is a top view of a portion of the prosthetic device shown in FIG. 1 taken at section line II—II.

Disposed between foot 14 and pylon 12 is means for indicating a predetermined force between foot 14 and pylon 12 and for permitting limited movement therebetween. In particular, a resilient member 46 abuts flange 16 and the upper portion 48 of foot 14. Imbedded in resilient member 46 are sensing elements such as first sensing element 50 and second sensing element 52. Sensing elements 50 and 52 lie in a sagittal plane passing through the axis A of pylon 12 with sensing element 50 anterior of axis A and sensing element 52 posterior of axis A. As can be seen in FIG. 3, sensing elements 50 and 52 are essentially normally open switches in a parallel arrangement in a sensing circuit 54. Positioned above each sensing element 50 and 52 is a set screw 56 and 58, respectively. Set screws 56 and 58 may be adjusted to preset the tension on normally open switches 50 and 52.

Referring to FIG. 3, it can be seen that sensing circuit 54 includes a power source 60 and an audible or visual alarm 62. Sensing elements 50 and 52 are in a parallel arrangement between leads 64 and 66, with lead 64 interconnected with power source 60 and lead 66 interconnected with alarm 62. Alarm 62 is in series with the parallel-arranged switches 50 and 52 such that closure of either switch 50 or switch 52 will activate alarm 62. It should be noted that sensing elements 50 and 52 are resiliently biased to the open position by resilient members 68. Rotation of the set screws 56 and 58 will partially close the normally open sensing circuits 50 and 52 such that an additional load imposed thereupon by an amputee through flange 16 will serve to close either or both of the sensing elements, thereby activating alarm 62.

OPERATION OF THE PREFERRED EMBODIMENT

In operation, the prosthesis acts as follows. Initially, it should be noted that cable 40 and resilient member 46 permit limited movement between foot 14 and pylon 12. Specifically, resilient member 46 in combination with the cable 40 absorbs shock and torque by permitting limited three axis rotation of the two elements about the joint therebetween. The shock associated by the heel contacting the walking surface would ordinarily be transmitted from foot 14 to pylon 12 and thence to the amputee's residual limb (not shown) to the detriment and possible discomfort of the amputee.

Assembly of the system is relatively straightforward and should be apparent to those skilled in the art. However, the following description is offered for clarity's sake. Pylon 12, which constitutes, in this instance, the lower limb of an amputee, is fitted with flange 16 in the manner shown in FIG. 1. The wedging member 22 of connector 20 is then inserted into bore 13 of pylon 12 with threaded member 34 loosely engaged in cylindrical member 24 as shown in FIG. 1. Cylindrical member 24 is then rotated to tighten the wedging member 22 into the bore 13 of pylon 12. At this time, the resilient member 46 along with the sensing elements 50 and 52 are positioned about connector 20 and foot 14 is threaded over cable 20. Sensing elements 50 and 52 should lie in a sagittal plane; hence, it is appropriate to include an indexing arrangement on resilient member 46 such as cavities 51 and 53 adjacent sensing elements 50 and 52. These cavities 51 and 53 may receive set screws 56 and 58. Nut 44 may then be positioned on threaded portion 42 and tightened to ensure a good fit between foot 14 and pylon 12. In order to prevent overtorquing of the connector 20, thereby eliminating the sensing capabilities of this invention, it may be necessary to measure the gap d between flange 16 and surface 48 for an initial setting.

However, it is equally possible to invert the prosthesis such that the foot is up with the pylon 12 positioned on a floor scale such as is ordinarily available in any medical facility. Pressure may then be applied to heel portion 70 or toe portion 72 while simultaneously reading the scale to determine the setting that will trigger alarm 62 at the heel down and toe off position of the gait of the amputee. Fine adjustment to this predetermined setting may be accomplished by rotating set screws 56 and 58, respectively. This fine tuning capability provides the prosthetist with an easy way to train an amputee without causing undue injury or trauma to the residual limb. If it becomes apparent that the amputee is applying excessive weight to the residual limb by the appearance of abcesses or the like, the alarm setting can be reduced to a lower force level such that the amputee can place more weight on the parallel bars ordinarily used in training or on crutches.

Other aspects, objects, and advantages of this invention may be obtained from a study of the drawings, the disclosure, and the appended claims.

What is claimed is:

1. A prosthesis comprising:
   a first member;
   a second member;
   means for interconnecting said first and said second members while allowing limited motion therebetween;
   said interconnecting means including a resilient member disposed between said first and second member;
   indicator means positioned in said resilient member for sensing a predetermined force between said first member and said second member.

2. The prosthesis of claim 1 wherein said indicator means includes adjustment means for varying the predetermined force.

3. The prosthesis of claim 1 wherein the interconnecting means includes flexible means for permitting limited motion between said first and said second members.

4. The prosthesis of claim 1 further including a flange affixed to said first member.

5. The prosthesis of claim 4 wherein the interconnecting means includes flexible means for permitting limited motion between said first and said second members.

6. The prosthesis of claim 4 wherein said first member is an endoskeletal prosthetic limb and said second member is a prosthetic foot.

7. The prosthesis of claim 1 wherein said interconnecting means further includes an elongated flexible member fixable at one end to said first member and fixable as its other end to said second member, said resilient member disposed around said flexible member, said flexible member formed to be placed under tension.

8. The prosthesis of claim 7 wherein said first member defines an axis and further wherein the indicator means includes a first sensing element and a second sensing element, each located in a sagittal plane passing through the axis of said first member, said first sensing element anterior of said first member axis and said second sensing element posterior of said first member axis.

9. The prosthesis of claim 8 wherein the indicator means includes a source of electrical energy and an audible alarm.

10. The prosthesis of claim 9 wherein each of said first and said second sensing elements is a pressure sensitive normally open switch.

11. The prosthesis of claim 10 wherein said indicator means further includes first and second variable adjustment means for placing said first and said second pressure sensitive switches under a predetermined load less than the load required to close said switches.

12. A pressure sensing system for a prosthesis, the prosthesis including a first member and a second member, the pressure sensing system comprising:
   means for interconnecting said first and said second members while allowing limited motion therebetween;
   said interconnecting means including a resilient member disposed between said first and second member;
   indicator means positioned in said resilient member for sensing a predetermined force between said first and said second member.

13. The pressure sensing system of claim 12 wherein said interconnecting means includes a flange affixed to one of said first and said second members.

14. The pressure sensing system of claim 13 wherein said interconnecting means further includes an elongated flexible member fixable at one end to said first member and fixable at its other end to said second member, said resilient member disposed around said flexible member, said flexible member formed to be placed under tension.

15. The pressure sensing system of claim 14 wherein said first member defines an axis and further wherein the indicator means includes a first sensing element and a second sensing element, each located in a sagittal plane passing through the axis of said first member, said first sensing element anterior of said first member axis and said second sensing element posterior of said first member axis.

16. The pressure sensing system of claim 15 wherein the indicator means further includes a source of electrical energy and an audible alarm.

17. The pressure sensing system of claim 16 wherein each of said first and said second sensing elements is a pressure sensitive normally open switch.

18. The pressure sensing system of claim 17 wherein said indicator means further includes first and second variable adjustment means for placing said first and said second pressure sensitive switches under a predetermined load less than the load required to close said switches.

* * * * *